(12) United States Patent
Xu (10) Patent No.: US 6,715,336 B1
(45) Date of Patent: Apr. 6, 2004

(54) PIEZOELECTRIC FORCE MOTION SCANNER

(75) Inventor: Ying Xu, Madison, WI (US)

(73) Assignee: nPoint, Inc., Madison, WI (US)

( * ) Notice: Subject to any disclaimer, the term of this patent is extended or adjusted under 35 U.S.C. 154(b) by 0 days.

(21) Appl. No.: 10/374,120

(22) Filed: Feb. 24, 2003

(51) Int. Cl.$^7$ .............................. G01N 3/56; G01M 7/04
(52) U.S. Cl. ................................................. 73/7; 73/577
(58) Field of Search ............................... 73/1, 577, 808, 73/815

(56) References Cited

U.S. PATENT DOCUMENTS

| | | |
|---|---|---|
| 5,700,093 A | 12/1997 | Hiramatsu et al. |
| 5,803,614 A | 9/1998 | Tsuji et al. |
| 5,969,226 A * | 10/1999 | Wert et al. ................ 73/7 |
| 6,315,455 B1 | 11/2001 | Tanaka et al. |
| 6,358,333 B1 | 3/2002 | Tanaka et al. |
| 6,416,228 B1 | 7/2002 | Müller et al. |
| 6,422,756 B1 | 7/2002 | Tanaka et al. |
| 6,601,456 B1 * | 8/2003 | Davidson et al. ........... 73/7 |

* cited by examiner

Primary Examiner—John E. Chapman
(74) Attorney, Agent, or Firm—Joseph T. Leone, Esq.; DeWitt Ross & Stevens S.C.

(57) ABSTRACT

Disclosed are a device and a corresponding method to test the fretting of a ball bearing under precisely controlled conditions. The device employs a first piezoelectric actuator to deliver a pre-determined force to the surface of a ball bearing or other object to be tested. The force is applied in a first axis of motion. A second piezoelectric actuator, coupled to a flexure hinge platform, translates the workpiece in a second axis of motion that is different (and preferably substantially orthogonal) to the first axis. The combination of the relative motion between the workpiece and the force exerted upon it produces predetermined dynamic patterns of the stress and strain on the surfaces of the workpiece being tested. Closed-loop control architecture, piezoelectric actuators, and force/displacement sensors included in the device provide highly accurate and rapid tests.

16 Claims, 7 Drawing Sheets

PIEZOELECTRIC FORCE MOTION SCANNER

FIELD OF THE INVENTION

The invention is directed to a device and corresponding method for testing materials for structural weakness. In the preferred embodiment, the invention is directed to a device and a method for testing ball and/or roller bearings to determine their tendency to experience fretting.

BACKGROUND OF THE INVENTION

Ball bearings and roller bearings are components that are used in vast array of machine tools and high-performance instruments. Bearings are found in an enormous variety of moving components, ranging in magnitude from heavy earth-moving equipment to delicate instruments such as disc drives, video tape recorders, and high-precision machine instruments. In short, the rolling contact bearing (i.e., ball bearings, roller bearings, and the like) is a fundamental element of machinery that, in many instances, determines the overall performance characteristics of the machine. If a particular bearing breaks or seizes, for example, not only is the individual segment or module wherein the bearing lies compromised, but the entire instrument is likely to cease functioning properly. Further, due to the very tight tolerances inherent in their function, if one bearing begins to break down or deform, it will generate intense friction and result in overheating which will degrade the race or track in which the bearing rides. This in turn will cause other bearings with which it is housed to become deformed, leading to a domino effect that rapidly affects the entire bearing assembly.

It follows from the above paragraph that the physical specifications of bearings are extremely important in manufacturing and maintaining precision instruments and machinery that have moving parts. In order to construct bearings and their races, and to keep them within precise tolerances over a defined period of time, a number of parameters must be monitored. These parameters include the specific dimensions of each bearing and its race, the hardness of those components, and their ability to withstand impact, resist corrosion, and resist distortion under load. Although all bearings become unserviceable over time due to wear, they may also become unserviceable because of seizing, breakage, undue wear or premature aging, false brinelling, flaking, and corrosion. Bearing failure can also be the result of rolling fatigue, incorrect selection, improper handling and/or improper maintenance, excessive load, poor shaft or housing accuracy, peeling, spalling, chipping, cracking, rust, corrosion, and fretting.

Many methods have been described to increase the life of bearings and decrease their incidence of breakdown. These include special alloys from which to fabricate the bearings (see, for example, U.S. Pat. Nos. 6,358,333; 6,422,756; and 6,315,455, all to Tanaka); use of ceramic bearings (see U.S. Pat. No. 6,416,228); use of silicon hybrids (see, for example, NSK Robust Series), as well as specific designs for the bearing structure itself (see U.S. Pat. Nos. 5,700,093 to Hiramatsu and 5,803,614 to Tsuji). Clearly, any method to optimize bearing performance must rely on tests to measure the physical characteristics of the bearing itself, both before and after the bearing has been put to its prescribed use.

Conventional methods to test bearing performance include simple performance verification tests wherein a prototype of the bearing is put through high pressure, high speed heavy duty use, etc., to verify bearing loss, seizure, and service life. (See, for example, Mitsubishi Heavy Industries, Ltd., Technical Rev. 39:26–30 (2002).) Other conventional means of testing bearing endurance include seizure tests wherein machinery is operated using the prototype bearing and the oil supply is curtailed while the machine continues to run. By measuring the oil flow and temperature, the response time required to save the system from breakdown can be determined. See SensIT Newsletter #3, June, 2001. Other means to test bearing breakdown include vibration testing to determine fretting resistance and impact resistance. All of these tests are implemented on bearing assemblies and the test conditions in local contact areas cannot be controlled precisely. Therefore, the failure modes of the bearings can only be investigated statistically.

Methods used to make conventional bearing assessments rely on mechanical mechanisms. Currently, conventional actuators, such as step motors, servo motors, and hydraulic or pneumatic actuators are used to deliver force or pressure in a test environment. A particular disadvantage when using conventional actuators is their poor dynamic response to a quick force change, especially under a heavy load.

More recently, electronic equipment and computer chips have been making use of piezoelectric devices as switches, thereby obviating the need for mechanical switches with their size and inherent error. The piezoelectric effect was first discovered when a pressure was applied to a quartz crystal and an electric charge in the crystal was created. It was later found that by applying an electric charge to the crystal the material would deform in shape in a standard degree. The first use of the piezoelectric effect was in ultrasonic submarine detectors developed during World War I. It was later found that barium titanate ceramics could be made which exhibited the piezoelectric phenomenon.

Because the tolerances of bearings are so precise and their proper action crucial to their operation, there is a need for the development of bearing test mechanisms that can apply force in a way that is controlled to deliver similar magnitude to a much more discrete area and measure the results on a nanoscale range. Further, because bearings are inherently moving parts, they are particularly subject to dynamic stress that can lead to fretting of the bearing.

Fretting is a form of adhesive wear; it occurs as the result of small scale oscillatory movements between the bearing and its housing. Typically fretting appears as highly polished regions on the bearing surface or as pockmarks on the bearing. Fretting is also accompanied by evidence of material movement between the housing and bearing back. Fretting occurs when there is unwanted relative movement between the bearing and housing. This movement can arise from any number of sources, such as an oversized housing, dirt or burrs on mating faces of the housing, insufficient bolt torque, deformation of the bearing under load, etc. Another cause is the flexibility of the bearing assembly itself. If the material from which the bearing and/or bearing race is assembled has inappropriate stiffness, the entire assembly may flex sufficiently under dynamic load to cause a relaxation of the radial interface and allow unwanted relative movement between the bearing and the race.

Fretting can eventually lead to overheating of the bearing material due to poor heat dissipation between the bearing back and the housing. This, in turn, leads ultimately to failure of the bearing entirely or generation of excessive heat that causes other components to fail.

The invention described herein was designed to investigate, measure, and otherwise quantify and/or qualify the fretting resistance of a bearing material. The invention is capable of controlling the load placed on a hearing while simultaneously subjecting the bearing to precisely controlled oscillatory movement. The invention thus yields superior dynamic results, and reduces the time-of-testing cycle significantly.

SUMMARY OF THE INVENTION

A first embodiment of the invention is directed to a device for testing the fretting of a bearing. In this embodiment, the device is dimensioned and configured so that a first object (e.g., a ball bearing) is urged against and dynamically translated, rotated, or otherwise urged against the surface of a second object (e.g., a flat plate of bearing housing material). In this embodiment of the invention, the device comprises a force scanner which comprises a first piezoelectric actuator. A workpiece holder is also optionally included, the workpiece holder being dimensioned and configured to hold a pre-selected workpiece securely and releasibly. (In the preferred embodiment, the workpiece holder is dimensioned and configured to hold a ball or roller bearing.) The force scanner is specifically dimensioned and configured to deliver a predetermined force to the bearing (i.e., the first object) in a first axis of motion (e.g., in the vertical direction). The predetermined force is generated by piezoelectric movement of the fist piezoelectric actuator.

The device further comprises a motion scanner. The motion scanner comprises a second piezoelectric actuator. The motion scanner is specifically dimensioned and configured to translate the second object in a second axis of motion, wherein the second axis of motion is different from the first axis of motion. In the preferred embodiment, the second axis of motion is substantially orthogonal to the first axis of motion. The translation of the second object is caused by piezoelectric movement of the second piezoelectric actuator. The first embodiment further comprises a first sensor operationally connected to the force scanner. The first sensor is capable of measuring the force delivered to the bearing by the force scanner and provides a feedback signal to a controller for a closed loop control (force control). A second sensor is operationally connected to the motion scanner. The second sensor is dimensioned and configured to measure the motion delivered to the second object by the motion scanner and to provide a feedback signal to the controller for a closed loop control (motion control).

As used herein, the term "operationally connected" designates that the recited elements are "connected" in a functional sense, meaning that, for example, the first sensor recited in the previous paragraph will function as a sensor because it is functionally connected, directly or indirectly, to the force scanner. Thus, elements that are "operationally connected"are not necessarily linked directly to one another, but may be separated by intervening elements that do not interfere with the operational relationship of the "operationally connected" elements.

A second embodiment of the invention is directed to a device for testing fretting of a bearing. In the second embodiment, the device comprises a force scanner including a first piezoelectric actuator, a first flexure stage, and a first cantilever. The first cantilever is interposed between the workpiece holder and the first piezoelectric actuator and is operationally connected to both the workpiece holder and the first piezoelectric actuator. The first cantilever is dimensioned and configured to amplify the motion generated by the first piezoelectric actuator. The amplification is to compensate for the force lost: (1) due to the compliance in the contact between the first and the second objects; and (2) due to wearing and the stiffness of the workpiece and the contact. The first flexure stage is dimensioned and configured to move in a first axis of motion and to resist motion in all other axes of motion. The force scanner as a whole is dimensioned and configured to deliver a predetermined force to the first object in the first axis of motion, the predetermined force being generated by piezoelectric movement of the first piezoelectric actuator and amplified by the first cantilever.

The second embodiment also includes a motion scanner that comprises a second piezoelectric actuator, a second flexure stage, and a second cantilever. The second cantilever is interposed between the second flexure stage and the second piezoelectric actuator and is operationally connected to both the second flexure stage and the second piezoelectric actuator. The second flexure stage is dimensioned and configured to move in a second axis of motion that is different from the firs axis of motion. In the preferred embodiment, the second axis of motion is substantially orthogonal to the first axis of motion. The second flexure stage is dimensioned and configured to resist motion in all other axes of motion. The second flexure stage is also dimensioned and configured to amplify the motion generated by the second piezoelectric actuator, to thereby achieve a longer scanning range in the second axis of motion. The motion scanner is dimensioned and configured to translate the second object in the second axis of motion, and wherein translation of the second object is caused by piezoelectric movement of the second piezoelectric actuator.

A first sensor is operationally connected to the force scanner. The first sensor is capable of measuring the force delivered to the object by the force scanner in the first axis of motion. A second sensor is operationally connected to the motion scanner. The second sensor is capable of measuring movement of the motion scanner in the second axis of motion. The outputs of both sensors are used to provide feedback for closed-loop control to achieve accuracy in the force and motion applied to the workpiece being tested. The closed loop control also serves to maximize accuracy in the phase matching between the applied force and the applied oscillating motion required by the testing.

The second embodiment of the invention further includes a closed-loop controller operationally connected to the first and second piezoelectric actuators. The controller is dimensioned and configured to independently control piezoelectric movement of the first and second piezoelectric actuators through a driver. The controller can be driven by a signal generator to control force applied by the force scanner, and translation of the motion scanner.

In this fashion, the system generates a precisely controlled, desired, and pre-determined contact force, friction force, and friction speed between the objects being tested. The force applied to the first object (i.e., the workpiece) in the first axis of motion is supplied by the force scanner. Movement of the motion scanner in the second axis of motion allows the device to produce relative motion and friction between the first object and the second object. The combination of the force and the motion scanners make it possible to simulate a wide variety of stress and strain conditions on the surfaces of the objects being tested. Thus, the invention enables objects to be tested for fretting (and other types of physical degradation and wear) in response to a known applied force, sliding velocity, distance, etc.

It is therefore an object of the present invention to provide a device and a corresponding method which can study and measure the effect of stresses, strains, and dynamic frictions on individual bearings and races. In a preferred embodiment of the invention, a Z-motion stage is designed to produce an accurately controlled contact force on the workpiece being tested. The friction force generated varies with the ambient operational conditions, such as the friction coefficient of the coupling materials, the friction velocity, the temperature, the lubricant, etc. The contact force is measured so that when the piezoelectric actuator of the Z-motion stage expands (i.e., in the first axis of motion), the first cantilever tilts downward, pivoted by a notch flexure at one end, and urges a first workpiece object (e.g., a bearing) against a second workpiece object (e.g., a race) on an X-motion stage. The reactive force on the first workpiece object is transferred to the force sensor mounted at the back of the workpiece holder of the Z-motion stage.

Note, however, that the friction force between the bearing and the race being tested will generate a bending moment on the first cantilever and be coupled into the force sensor due to the position offset between the friction force and force sensor. Unless accounted for, this bending moment will degrade the accuracy of the force control.

Thus, in order to decouple the crosstalk of friction force, and thereby improve the accuracy of the present invention, a flexure decoupling mechanism (i.e., means for decoupling frictional crosstalk) may optionally be interposed between the workpiece holder and the force sensor. The decoupling mechanism is dimensioned and configured to have a very low stiffness in the first axis of motion (to thereby maintain the sensitivity of the force sensor) and an extremely high stiffness in all other axes to decouple all the forces and moments except the force applied in the first axis of motion.

The force applied by the Z-motion stage (in the first axis of motion) is detected by a strain gauge sensor or any other suitable means for detecting a force applied to an object. The movement of the X-motion stage (in the second axis of motion) is detected by a capacitance sensor or any other suitable means for detecting motion. The output signals of the sensors are then amplified via suitable amplification circuitry and displayed using any means for display now known or developed in the future, such as an analog or digital meter, oscilloscope, light-emitting diode display, liquid crystal display, cathode ray tube display, and the like.

The primary advantage of the present invention is that it allows bearings, races, and other workpieces subject to dynamic stress and strain to be tested quickly and confidently, with unparalleled precision and accuracy. Moreover, it allows the workpieces to be tested systematically, in isolation, and under test conditions that can be completely controlled. Thus, using the present invention, bearings, races, and other workpieces can be tested under precisely known applied forces, at known temperatures, with well-controlled force-motion patterns, etc. The novel design of the flexure platform and the associated piezoelectric controls and sensor electronics enables fretting tests that were previously difficult or impossible to be conducted individually, to be conducted quickly, reproducibly, and with unprecedented control. This greatly improves the selection of appropriate bearing materials for any given purpose. As a result, the operational life span of the bearing assembly (or other friction-bearing surface), once placed into service, is greatly extended.

DETAILED DESCRIPTION OF THE INVENTION

Figure 1:
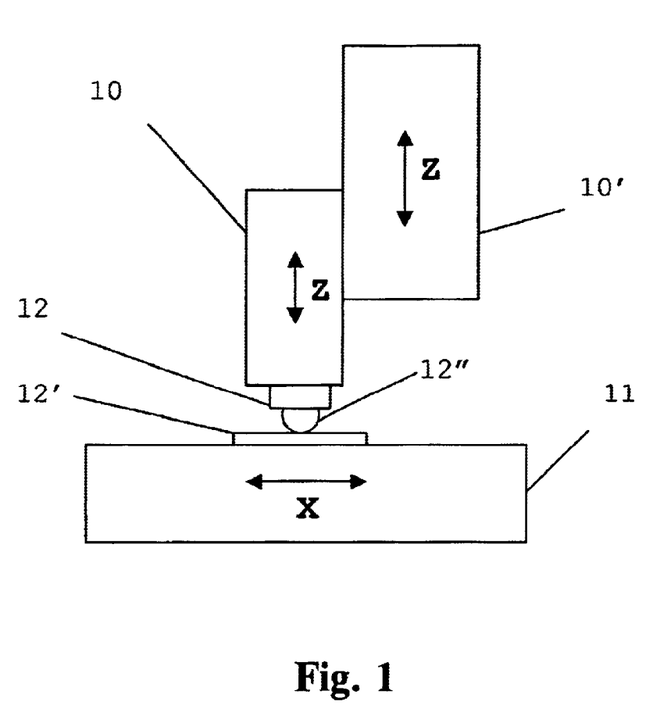
FIG. 1 is a schematic diagram of the preferred embodiment of a device according to the present invention; the Z-stage 10 represents the force scanner and the X-stage 11 represents the motion scanner.

The present invention is directed to a device that is designed for fretting tests of ball bearing materials (and any other friction-bearing surface) under various controlled conditions. Referring now to FIG. 1, the device comprises a force scanner 10 that applies a force of known magnitude to the workpiece in a first axis of motion. As shown in FIG. 1, the force scanner 10 moves in the Z-plane. The device further comprises a motion scanner 11 that moves in a second axis of motion that is different from the first axis of motion. As shown in FIG. 1, the motion scanner 11 moves in the X-plane. The combination of force and motion generates friction between the workpieces 12' and 12".

The force scanner and motion scanner are driven by piezoelectric elements whose output can be compiled to yield data that relate applied force and friction motion to fretting of the workpiece. A coarse-positioning stage 10', a sample holder 12, and a frame (not shown) are also provided to position the workpiece and to hold the workpiece in the desired orientation.

Referring now to FIG. 1, there is illustrated schematically a preferred embodiment of the present invention. As shown in FIG. 1, the device comprises a force scanner 10, that is dimensioned and configured to apply a force of known magnitude to a ball bearing workpiece 12" and race 12'. The force applied by the force scanner can be constant or variable. As shown in FIG. 1, the force scanner 10 applies a force in the vertical direction, which has been arbitrarily designated in the figure as the Z axis. A coarse-positioning stage 10' supports the force scanner and brings the bearing ball workpiece 12" into contact with the race material workpiece 12' in advance of the force scanner applying any force to the workpieces. The coarse-positioning stage can be driven manually or by a conventional actuator, such as a step motor, a servo motor, or a hydraulic or pneumatic actuator. A motion scanner 11, on which the second workpiece 12' is mounted, is shown as being free to move in the X axis.

In the preferred embodiment, the force scanner 10 and the motion scanner 11 are both driven by piezoelectric actuators. The axis of motion of the force scanner, as compared to the axis of motion in the motion scanner, is one key to the high degree of accuracy and precision that can be obtained using the present device. As shown in FIG. 1, the force scanner 10 is preferably a piezoelectric-driven Z-actuator that is designed to transfer the force generated by the piezoelectric actuator to the workpiece precisely and efficiently. The force scanner is dimensioned and configured to move very smoothly, with very low stiffness and a minimal amount of friction, in only the first axis of motion (the Z-direction as depicted in FIG. 1). Therefore a flexure mechanism is used which is dimensioned and configured to be very flexible in the Z axis, but extremely stiff in all other directions, including rotational motion. The stiffness of the force scanner in the Z axis depends essentially entirely upon the stiffness of the piezoelectric actuator used to drive the force scanner.

The motion scanner 11 is preferably a piezoelectric-driven flexure stage that is designed to move very smoothly, with very low stiffness and a minimal amount of friction, in only the second axis of motion (the X direction as shown in FIG. 1). The second axis of motion is non-colinear with the first axis and is preferably substantially orthogonal to the first axis of motion. The motion scanner 11 is dimensioned and configured to be extremely stiff in all other directions, including rotation. (That is, the motion scanner is designed to minimize roll, pitch, and yaw.) For the force scanner 10 to generate sufficient force, the motion scanner 11 must be extremely stiff in the first axis of motion (the vertical direction as shown in FIG. 1).

Figure 2:
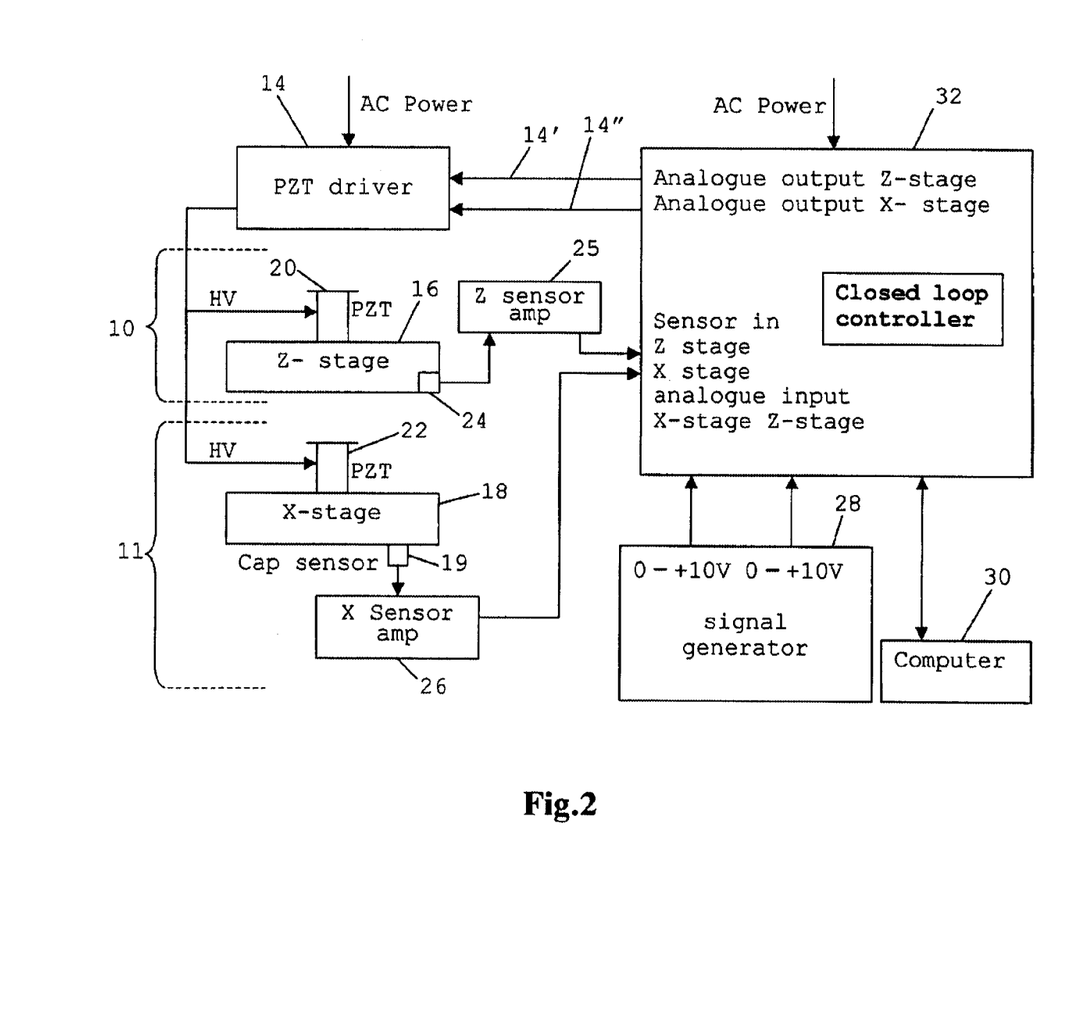
FIG. 2 is a schematic representation of the preferred control circuitry for use in a device according to the present invention.

FIG. 2 illustrates, in schematic, a preferred closed-loop control circuit to be used in conjunction with the force scanner and motion scanner, as well as the interrelationship between the scanners and the control circuitry. As shown in FIG. 2, the force scanner 10 (see FIG. 1) comprises a first piezoelectric actuator 20, operationally connected to a Z-motion stage 16. Means 24 for sensing force exerted upon the stage 16 is provided. These means for sensing force, referred to hereinafter as force sensor means 24, is preferably a strain gauge force sensor that will generate an electrical signal that can be correlated to the force exerted upon the stage 16 by the actuator 20. The signal generated by the force sensor means 24 is transmitted to amplifier 25, and ultimately to controller 32 as the feedback or monitoring signal. As noted above, the Z-motion stage 16 of the force scanner 10 has a very high stiffness in all axes except the Z axis.

The signal generated by the force sensor means 24 and amplified by the amplifier 25 is transmitted to the controller 32. The controller is preferably a PID-type controller (see below), and the force data encoded by the signal generated by force sensor means 24 can be used in a feedback loop within the controller to guide further manipulations of the actuator 20. Another feedback loop can be used with the signal generated by motion sensor means 19 to guide further manipulations of the actuator 22 (see next paragraph).

The motion scanner 11 (see FIG. 1) comprises a second piezoelectric actuator 22 operationally connected to an X-motion-stage 18. In the same fashion as the force scanner, means 19 for sensing motion of the stage 18 is provided. These means are referred to hereinafter as motion sensor means 19. The motion sensor means 19 is preferably a capacitance sensor or other motion sensor that generates an electrical signal that is correlatable to the X-axis motion exerted by the actuator 22 on the stage 18. The signal generated by the motion sensor means 19 is transmitted to amplifier 26, and ultimately to controller 32. As noted above, the X-motion stage 18 of the motion scanner 11 has a very high stiffness in all axes except the X axis. In this fashion, the Z-axis motion of the force scanner 10 is decoupled from the X-axis motion of the motion scanner 11.

The first piezoelectric actuator 20 and the second piezoelectric actuator 22 are operationally connected to, and controlled by, means for driving a piezoelectric element 14 (referred to hereinafter as the driver). The driver 14 supplies electric voltage to the piezoelectric actuators 20 and 22, thereby causing the actuators to expand or contract in a controlled fashion, and thereby driving their respective stages, 16 and 18. Suitable piezoelectric drivers are commercially available. For example, Nagano Keiki Co., Ltd., (Higashimagome Ohta-Ku, Tokyo, Japan) and LTG Lasertech Group (Mississauga, Ontario L5S 1V1, Canada) both manufacture and market drivers that can be used in the present invention.

The force scanners for use in the present invention preferably have a working bandwidth greater than 10 Hz, and are capable of applying a force in excess of 100 N to the workpieces. It is preferred that the stroke of the force scanner be greater than approximately 200 micrometers.

The controller 32 is preferably a PID type (proportional, integral, derivative) controller. Such controllers are commercially available from a number of sources, including Honeywell (the UDC series), Modicon (models 584 and 984), and General Electric/Fanuc.

A programmable signal generator 28 may optionally be included to generate applied force and motion patterns (for the force scanner and the motion scanner, respectively). Suitable signal generators for use in the present invention are commercially available from a number of sources, including HP/Agilent and General Electric/Fanuc. Instructions can be programmed into the controller 32 and data collected from the controller using computer 30.

By way of example, the signal generator 28 can be used to program and generate a wave pattern which is transmitted to the controller 32. The predetermined wave pattern thus provides the instructions which are then directed by the controller to the driver 14 via operational connectors 14' and 14". The driver, in turn, drives the piezoelectric actuators 20 and 22 according to the preselected wave pattern. The controller transmits a wave pattern for the force scanner, as well as the motion scanner, via operational connectors represented schematically at 14' and 14" in FIG. 2.

Figure 3:
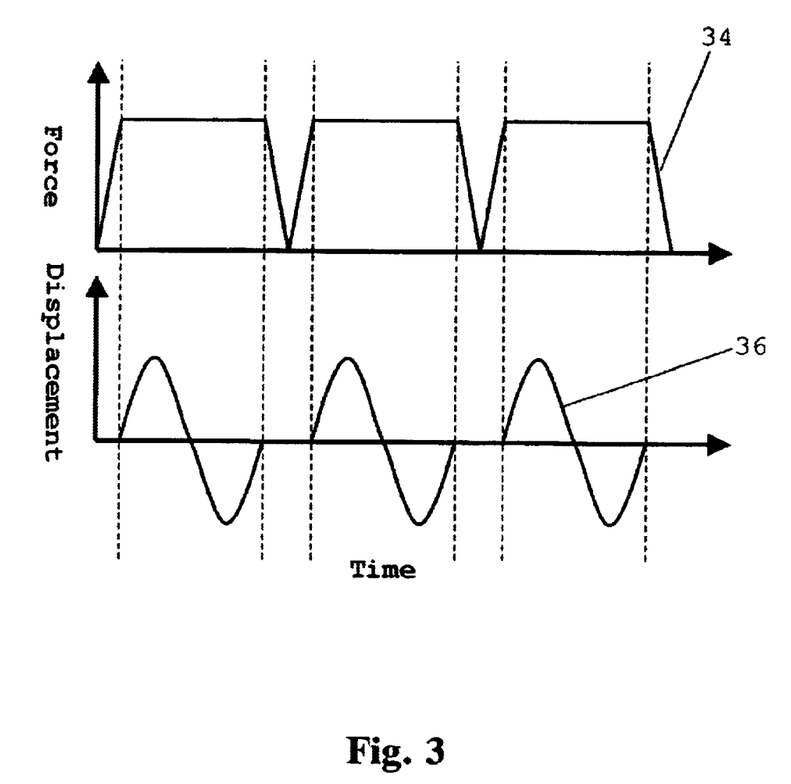
FIG. 3 is a representative example of one type output generated by the present invention. Here, the output is depicted as a scanning pattern of the force 34 applied to the workpiece and the motion exerted and detected 36 by the system.

FIG. 3 illustrates a typical wave pattern that can be generated by the signal generator 28. This pattern is strictly for illustration only. A vast number of different wave patterns can be generated. Trace 34 represents the force applied upon the workpiece in the Z-axis. In trace 34, the abscissa represents time and the ordinate represents applied force. Thus, trace 34 represents the signal transmitted from the controller 32, to the driver 14, and then to the actuator 20, which thereby drives the stage 16.

Similarly, trace 36 represents the displacement in the X-axis of the stage 18. In trace 36, the abscissa again represents time, but the ordinate represents displacement of the stage 18 in the X-axis. Thus, trace 36 represents the signal transmitted from the controller 32, to the driver 14, and then to the actuator 22, which thereby drives the stage 18.

Combining the two traces 34 and 36 thus yields a wave pattern wherein a constant force is first applied to the bearing in the Z-axis. This force is represented by the flat plateaus in trace 34. Once the force has reached the desired magnitude, the stage 18 is then oscillated back and forth in the X-axis. This oscillatory movement is represented by the sinusoidal wave shown in trace 36. Once the stage 18 has moved back and forth through one complete cycle, the applied force is allowed to go to zero. This is represented by the sharply pointed valleys in trace 34. The entire wave pattern is then repeated as often as is desired: the force is first applied to the workpiece, the stage 18 is cycled back and forth, and the force is then removed. Note that the wave patterns depicted in FIG. 3 are strictly for illustration purposes only and do not limit in any fashion the wave patterns that can be generated by the present invention.

Clearly, one of skill in the art can envision a virtually unending series of wave patterns. Selection of an appropriate wave pattern is dictated by the workpiece being tested, the materials from which the workpiece is made, the ultimate use to which the workpiece will be put, etc. Those skilled in the art of testing load-bearing surfaces are capable of selecting a wave pattern that is appropriate for any given workpiece.

Figure 4:
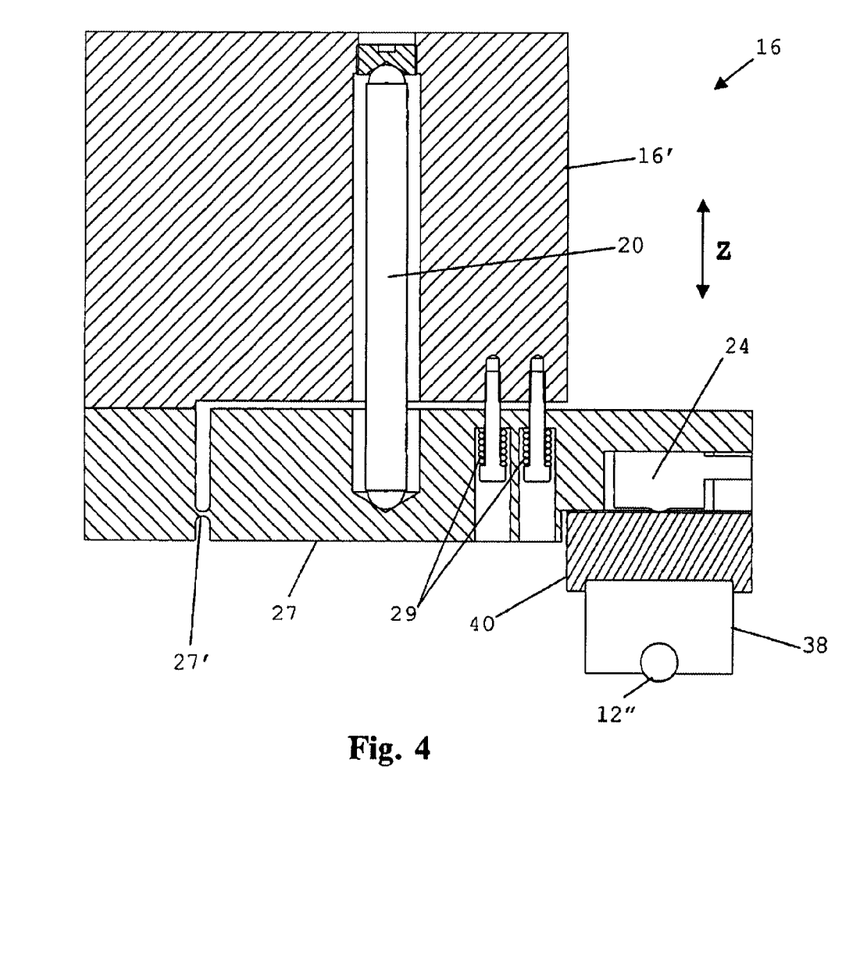
FIG. 4 is a schematic rendering of a portion of the force scanner (shown schematically as reference numeral 10 in FIG. 1).

FIG. 4 is a schematic illustration of the force scanner 10 (as depicted in FIG. 1). This figure illustrates the Z-motion stage body 16', which is connected to the first cantilever 27 by a notch flexure 27'. Preload springs 28 provide a preload to the piezoelectric actuator 20 through the cantilever. A load sensor 24 is operationally disposed between the cantilever 27 and the force decoupling mechanism 40, which is designed to allow only vertical force to be transferred to the load sensor 24 from the workpiece 12. (See also FIG. 5 and the discussion that follows.) The sensor 24 generates an electrical signal that can be correlated to the amount of force exerted by the stage 16' on the workpiece 12.

Further shown in FIG. 4 is a workpiece holder 38 (corresponds to reference numeral 12 in FIG. 1), in which is immobilized a ball bearing workpiece 12". The holder 38 is dimensioned and configured to immobilize the workpiece 12" firmly and releasibly. As shown in FIG. 4, the workpiece holder is dimensioned and configured to immobilize a spherical ball bearing. This is for purposes of illustration only. The sample holder can be dimensioned and configured to accommodate a workpiece of literally any physical geometry.

Figure 5:
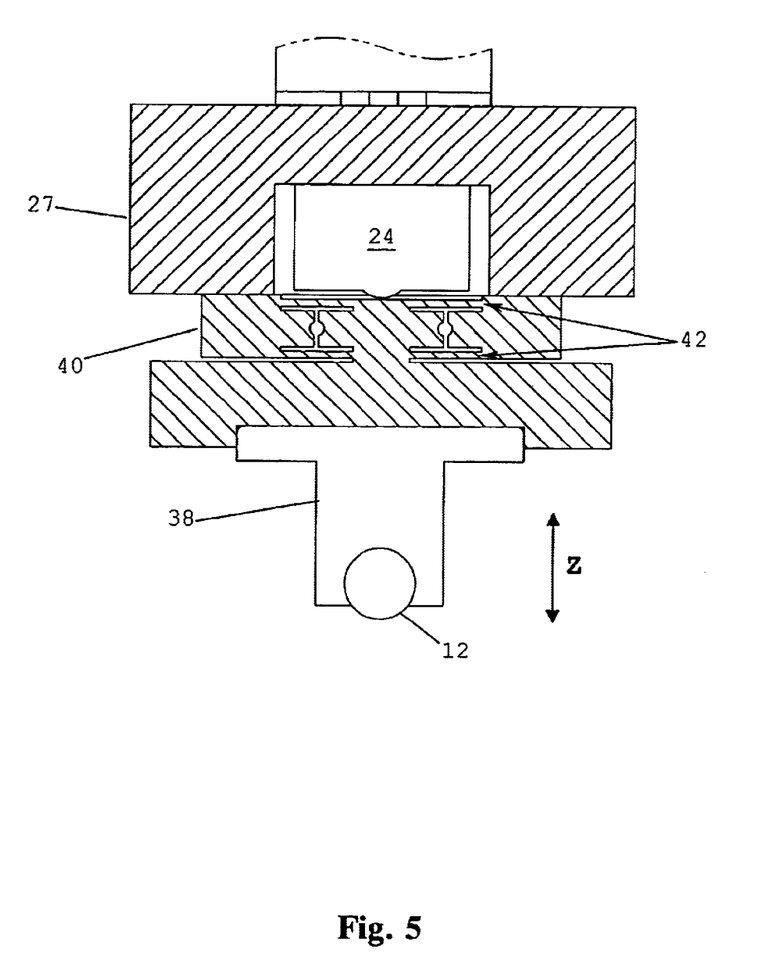
FIG. 5 is a schematic of the force sensor assembly (shown schematically as reference numeral 24 in FIG. 4) and the crosstalk decoupling mechanism (shown schematically as reference numeral 16' in FIG. 4).

Referring now to FIG. 5, the sample holder 38 is fixed (either releasibly or permanently) to the force decoupling mechanism 40, which is in turn fixed (either releasibly or permanently) onto the cantilever 27. Flexures 42 (see FIG. 5) are designed into the force decoupling mechanism 40, so as to permit force in the first axis of motion only (i.e., force in only the Z-axis as shown in the figures) to be transferred to the load sensor 24. The flexures are designed, using finite analysis, so as to minimize any non-Z-axis movement due to friction force or bend moment. In operation, the lower surface of the ball bearing workpiece 12" as shown in FIGS. 4 and 5 would be in contact with a second workpiece 12' (such as a ball bearing race, see FIG. 1) on the motion scanner 11 (see FIG. 1).

Figure 6:
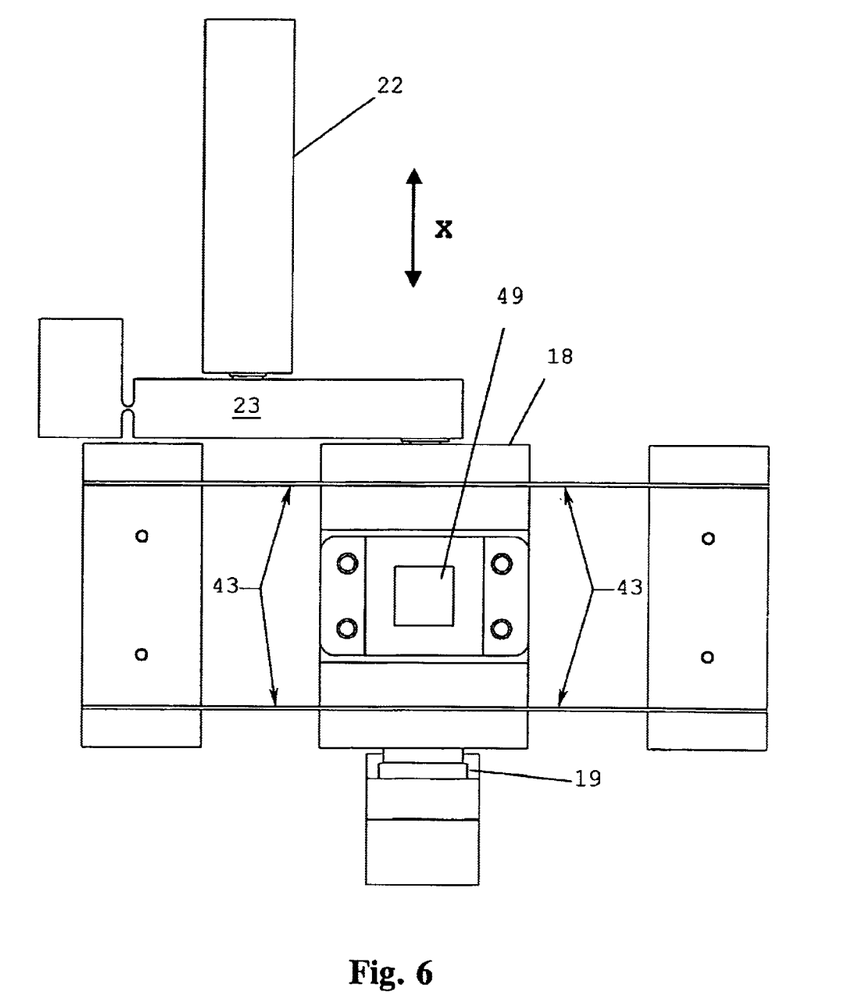
FIG. 6 is a top plan schematic of the motion scanner (depicted schematically as reference numeral 11 in FIG. 1).

A top plan schematic view of the motion scanner 11 is shown in FIG. 6. As illustrated, a second workpiece, such as a ball bearing race, rests on a second sample holder 49, which is in turn mounted (permanently or releasibly on the X-motion stage 18. As shown in FIG. 6, the stage moves in the X-axis by means of flexures 43. The flexures are designed to allow motion of the stage only in the X-axis (i.e., only in the second axis of motion), while simultaneously minimizing motion of the stage in all other axes. The flexure mechanism is dimensioned and configured to provide smooth motion of the stage, without friction in motion translation.

As shown in FIG. 6, the second piezoelectric actuator 22 is operationally connected to an X-motion cantilever 23. The cantilever, in turn, is operationally connected to the motion stage 18. The cantilever functions to amplify the motion of the piezoelectric actuator 22, and thereby drive the X-axis motion of stage 18. A similar cantilever arrangement is also used to drive the force scanner, as discussed earlier (see FIG. 4).

Figure 7:
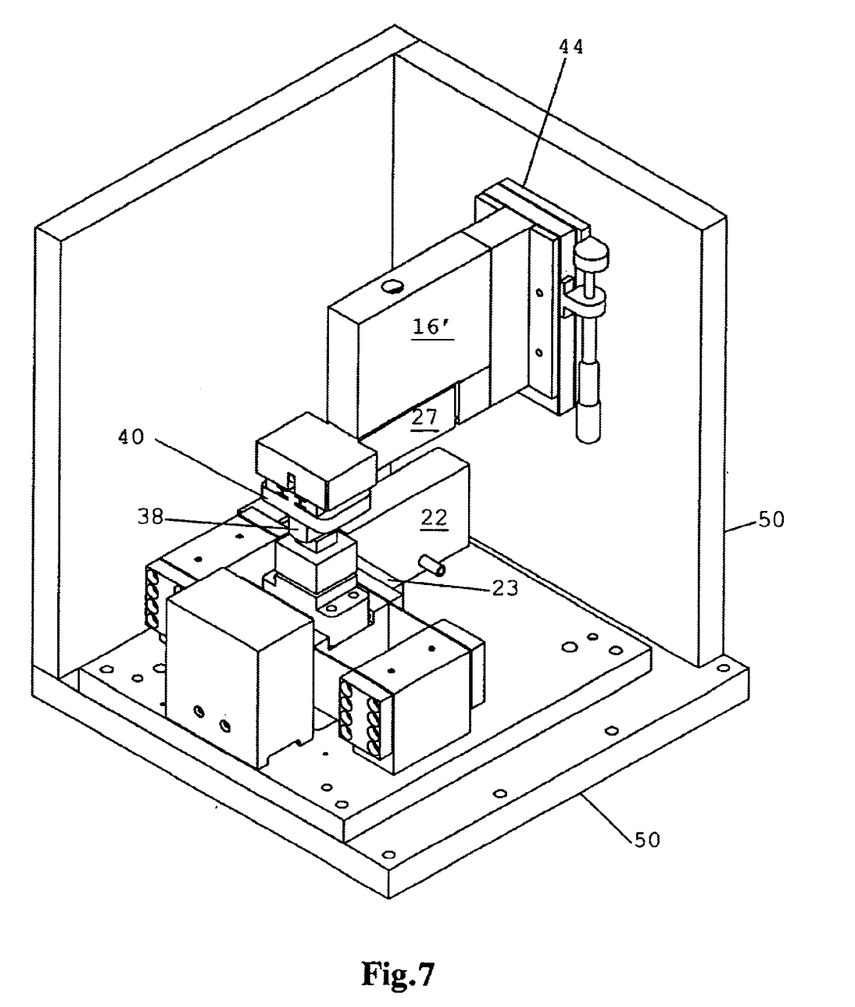
FIG. 7 is a partial cut-away, perspective rendering of a device according to the present invention.

A partial cut-away, perspective view of a device according to the present invention is depicted in FIG. 7. FIG. 7 depicts the second piezoelectric actuator 22 operationally connected to the X-motion cantilever 23, as described in the previous paragraph. Also shown are the Z-motion stage body 16' (with the piezoelectric actuator 20 embedded inside) and a corresponding Z-motion cantilever 27 that functions to amplify the Z-axis movement of the actuator 20. The cantilever 27 is operationally connected to the force decoupling mechanism 40 and workpiece holder 38. A coarse-positioning stage 44 is also shown on which the Z stage body 16' is mounted. The coarse-positioning stage 44 carries the Z scanner body 16' vertically (as shown in FIG. 7) to bring the workpieces on the force scanner and motion scanner into contact with each other before scanning. The entire device is immobilized (reversibly or permanently) upon frame 50 so as to provide a non-movable origin for the apparatus.

It is understood that the invention is not confined to the particular construction and arrangement of parts herein illustrated and described, but embraces such modified forms thereof as come within the scope of the following claims.

What is claimed is:

1. A device for testing wear of a ball bearing or other workpiece, the device comprising:
    a force scanner comprising a first piezoelectric actuator, wherein the force scanner is dimensioned and configured to deliver a predetermined force to a workpiece in a first axis of motion, and wherein the predetermined force is generated by movement of the first piezoelectric actuator;
    a motion scanner comprising a second piezoelectric actuator, wherein the motion scanner is dimensioned and configured to translate the workpiece in a second axis of motion that is different from the first axis of motion, and wherein translation of the workpiece is caused by movement of the second piezoelectric actuator; and
    a first sensor operationally connected to the force scanner, the first sensor capable of measuring the force delivered to the workpiece by the force scanner in the first axis of motion; and
    a second sensor operationally connected to the motion scanner, the second sensor capable of measuring translation of the workpiece by the motion scanner in the second axis of motion.

2. The device of claim 1, wherein the motion scanner is dimensioned and configured to translate the workpiece in a second axis of motion that is substantially orthogonal to the first axis of motion.

3. The device of claim 1, further comprising a driver operationally connected to the first and second piezoelectric actuators, wherein the driver is dimensioned and configured to independently control piezoelectric movement of the first and second piezoelectric actuators.

4. The device of claim 3, further comprising a programmable signal generator operationally connected to the driver, wherein the signal generator is programmable to control force applied by the force scanner, and translation of the motion scanner.

5. The device of claim 1, further comprising a controller, the controller comprising a driver, a programmable signal generator, and means for amplifying signals from the first and second sensors, wherein the controller is operationally connected to the first and second piezoelectric actuators and the first and second sensors, and further wherein the driver is dimensioned and configured to independently control piezoelectric movement of the first and second piezoelectric actuators in response to command signals generated by the signal generator and feedback signals generated by the first and second sensors.

6. The device of claim 1, wherein the force scanner further comprises a first flexure stage operationally connected to the first piezoelectric actuator, wherein the first flexure stage is dimensioned and configured to move in the first axis of motion and to resist motion in all other axes of motion.

7. The device of claim 6, further comprising a first cantilever, wherein the first cantilever is operationally interposed between the first flexure stage and the first piezoelectric actuator.

8. The device of claim 7, further comprising a force decoupling mechanism, wherein the force decoupling mechanism is interposed between the workpiece and the first cantilever, wherein the force decoupling mechanism is dimensioned and configured to transfer force applied by the force scanner to the workpiece in the first axis and to decouple any forces exerted in all other axes of motion.

9. The device of claim 1, wherein the motion scanner further comprises a second flexure stage operationally connected to the second piezoelectric actuator, wherein the second flexure stage is dimensioned and configured to move in the second axis of motion and to resist motion in all other axes of motion.

10. The device of claim 9, further comprising a second cantilever, wherein the second cantilever is interposed between the second flexure stage and the second piezoelectric actuator and operationally connected to both the second flexure stage and the second piezoelectric actuator.

11. The device of claim 1, wherein the force scanner further comprises a first flexure stage and a first cantilever, wherein the first cantilever is operationally interposed between the first flexure stage and the first piezoelectric actuator, and wherein the first flexure stage is dimensioned and configured to move in the first axis of motion and to resist motion in all other axes of motion; and wherein the motion scanner further comprises a second flexure stage and a second cantilever, wherein the second cantilever is interposed between the second flexure stage and the second piezoelectric actuator and operationally connected to both the second flexure stage and the second piezoelectric actuator, and wherein the second flexure stage is dimensioned and configured to move in the second axis of motion and to resist motion in all other axes of motion.

12. A device for testing fretting of a ball bearing, the device comprising:

a force scanner comprising a first piezoelectric actuator, a first flexure stage, and a first cantilever, wherein the first cantilever is operationally interposed between the first flexure stage and the first piezoelectric actuator and is operationally connected to both the first flexure stage and the first piezoelectric actuator, and wherein the first flexure stage is dimensioned and configured to move in a first axis of motion and to resist motion in all other axes of motion, and wherein the force scanner is dimensioned and configured to deliver a predetermined force to a ball bearing workpiece in the first axis of motion, the predetermined force being generated by movement of the first piezoelectric actuator;

a motion scanner comprising a second piezoelectric actuator, a second flexure stage and a second cantilever, wherein the second cantilever is interposed between the second flexure stage and the second piezoelectric actuator and is operationally connected to both the second flexure stage and the second piezoelectric actuator, and wherein the second flexure stage is dimensioned and configured to move in a second axis of motion that is substantially orthogonal to the first axis of motion and to resist motion in all other axes of motion, and wherein the motion scanner is dimensioned and configured to translate the workpiece in the second axis of motion, and wherein translation of the workpiece is caused by movement of the second piezoelectric actuator;

a first sensor operationally connected to the force scanner, the first sensor capable of measuring the force delivered to the workpiece by the force scanner and movement of the force scanner in the first axis of motion;

a force decoupling mechanism, wherein the force decoupling mechanism is interposed between the workpiece and the first cantilever, wherein the force decoupling mechanism is dimensioned and configured to transfer force applied by the force scanner to the workpiece in the first axis and to decouple any forces exerted in all other axes of motion; and a second sensor operationally connected to the motion scanner, the second sensor capable of measuring movement of the motion scanner in the second axis of motion.

13. The device of claim 12, further comprising a controller, the controller comprising a driver, a programmable signal generator, and means for amplifying signals from the first and second sensors, wherein the controller is operationally connected to the first and second piezoelectric actuators and the first and second sensors, and further wherein the driver is dimensioned and configured to independently control piezoelectric movement of the first and second piezoelectric actuators in response to command signals generated by the signal generator and feedback signals generated by the first and second sensors.

14. A method for wear testing a workpiece, the method comprising:

(a) delivering a predetermined force to a workpiece in a first axis of motion, wherein the predetermined force is generated by movement of a first piezoelectric actuator, (b) translating the workpiece in a second axis of motion, wherein the second axis of motion is substantially orthogonal to the first axis of motion, and wherein translation of the workpiece is caused by movement of a second piezoelectric actuator, and (c) cycling the predetermined force delivered to the workpiece in step (a) and cycling the translation of the workpiece in step (b) in a predetermined pattern to simulate dynamic stress and strain on the workpiece.

15. The method of claim 14, wherein in step (a) the first piezoelectric actuator is urged against a first cantilever, which first cantilever is thereby urged against a first flexure stage, wherein the first flexure stage is dimensioned and configured to move in the first axis of motion and to resist motion in all other axes of motion.

16. The method of claim 14, wherein in step (b), the second piezoelectric actuator is urged against a second cantilever, which is thereby urged against a second flexure stage, and wherein the second flexure stage is dimensioned and configured to move in the second axis of motion and to resist motion in all other axes of motion.

* * * * *